United States Patent [19]

Mikitenko et al.

[11] 4,366,032
[45] Dec. 28, 1982

[54] PROCESS FOR PRODUCING DEHYDRATED ALCOHOLS FOR USE AS COMPONENT OF A MOTOR FUEL COMPOSITION

[75] Inventors: Paul Mikitenko, Noisy Le Roi; Lionel Asselineau, Paris, both of France

[73] Assignee: Institut Francais du Petrole, Rueil-Malmaison, France

[21] Appl. No.: 298,432

[22] Filed: Sep. 1, 1981

[30] Foreign Application Priority Data

Sep. 1, 1980 [FR] France ................................ 80 18901

[51] Int. Cl.³ ........................ B01D 3/40; C07C 29/84
[52] U.S. Cl. ........................................ 203/18; 203/19; 203/58; 203/59; 203/64; 203/84; 203/DIG. 13; 44/56
[58] Field of Search ........................ 203/18, 19, 58, 59, 203/64, 84, 78, 79, 85, DIG. 13; 426/493, 494; 568/916; 44/56

[56] References Cited

U.S. PATENT DOCUMENTS

| | | | |
|---|---|---|---|
| 2,392,534 | 1/1946 | Von Keussler | 203/84 |
| 2,551,584 | 5/1951 | Carlson et al. | 203/84 |
| 2,552,412 | 5/1951 | Drout et al. | 203/84 |
| 2,559,519 | 7/1951 | Smith et al. | 203/84 |
| 2,570,205 | 10/1951 | Carlson et al. | 203/84 |
| 2,591,671 | 4/1952 | Catterall | 203/19 |
| 2,591,672 | 4/1952 | Catterall | 203/18 |
| 2,595,805 | 5/1952 | Morrell et al. | 203/84 |
| 2,614,971 | 10/1952 | Burton | 203/18 |
| 2,993,840 | 7/1961 | Poincet | 203/84 |
| 3,990,952 | 11/1976 | Katzen et al. | 203/84 |

Primary Examiner—Wilbur L. Bascomb, Jr.
Attorney, Agent, or Firm—Millen & White

[57] ABSTRACT

Process for dehydrating aliphatic alcohols admixed with water wherein the alcohols-water mixture is subjected to a first fractionation in the presence of a selective solvent, giving a vapor effluent containing dehydrated light alcohols and a liquid phase containing heavy alcohols, water and the selective solvent, said liquid phase being subjected to a second fractionation giving as vapor effluent an hetero-azeotropic mixture of water and heavy alcohols and, as liquid effluent, the selective solvent, which is fed back, said hetero-azeotropic mixture being condensed and separated into:

(a) a light phase of high alcohol content which is subjected to a third fractionation giving a vapor effluent which is fed back and dehydrated heavy alcohols as liquid effluent, and (b) a heavy phase which is subjected to a fourth fractionation giving a vapor effluent which is fed back and water as liquid effluent.

10 Claims, 1 Drawing Figure

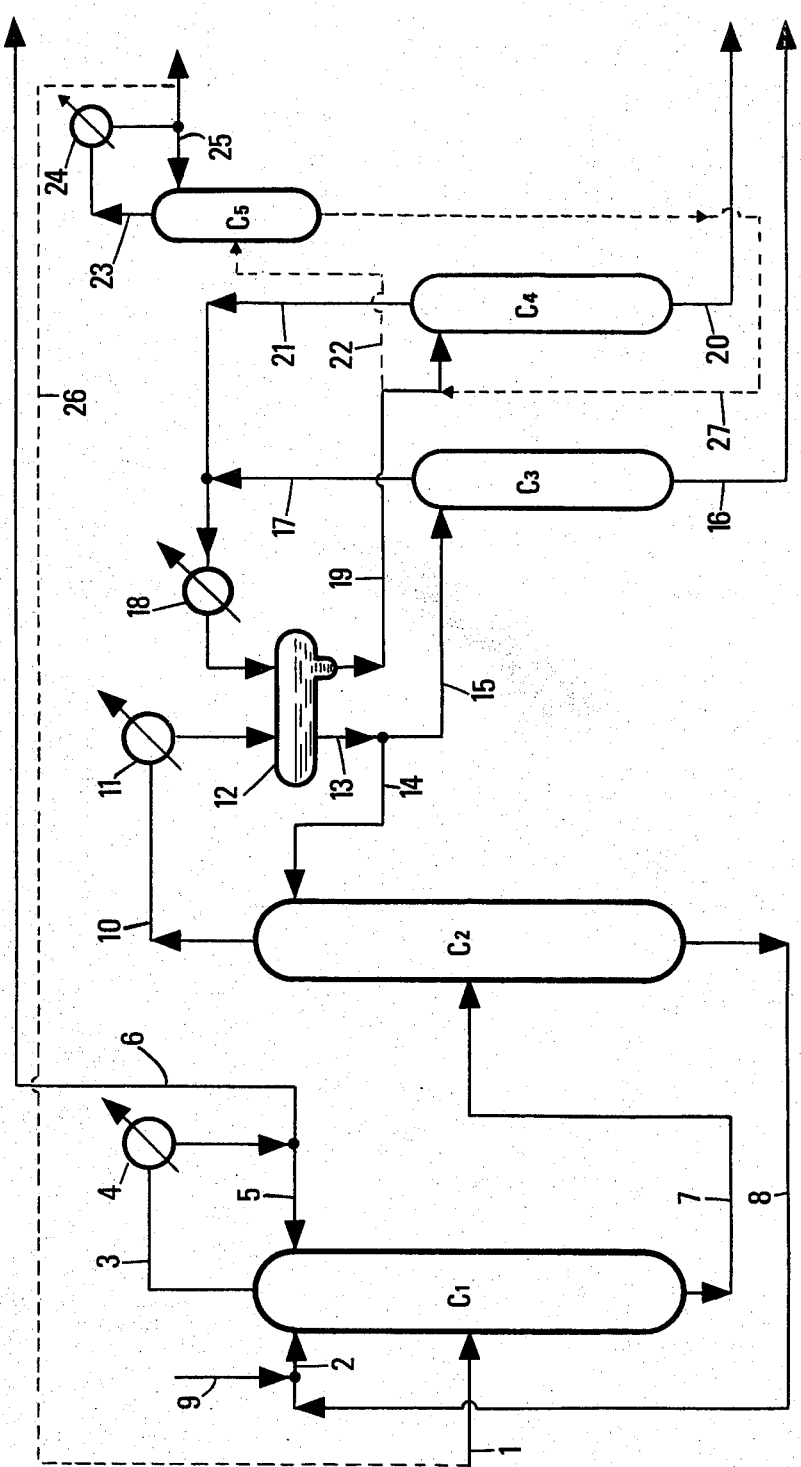

PROCESS FOR PRODUCING DEHYDRATED ALCOHOLS FOR USE AS COMPONENT OF A MOTOR FUEL COMPOSITION

The invention concerns a process for producing dehydrated alcohols for use either as such or as components of a motor fuel. More particularly, it concerns the production of water-free alcohols by extractive distillation of a mixture of alcohols and water in the presence of selective solvents.

Synthesis aliphatic alcohols are produced by different processes. They are obtained in particular by catalytic synthesis from CO and $H_2$, by partial oxidation of hydrocarbons or by fermentation of sweet juices. The obtained raw product contains small amounts of organic by-products (ethers, ketones, aldehydes) together with water in variable amounts, for example from 10 to 90% by weight.

The use of alcohols as motor fuel in admixture with gasoline requires dehydrated alcohols having a residual water content generally lower than 2% by weight, which must be obtained unexpensively. The use of alcohols has been proposed to cope with the shortage and the present high price of the petroleum products. Moreover, the alcohols have an antiknock property so that it is possible to reduce to a large extent the lead content of premium gasoline, and accordingly, to reduce the atmospheric pollution. The drying of these alcohol mixtures cannot be effected by mere distillation in view of the formation of azeotropes between water and the aliphatic alcohols, except methanol.

Various methods have been proposed to dry mainly ethanol. The azeotropic distillation making use of a satured or aromatic or naphthenic hydrocarbon or a mixture thereof as stripping agent is used in various installations. There is formed a water/hydrocarbon/alcohol azeotrope which distills at the top of the column, is condensed and them partially recycled and partially treated in a second column; anhydrous alcohol is recovered in the lower part of the column. However benzene, in most cases used for drying ethanol, has the disadvantage of being toxic and the apparent simplicity of the method is compensated by the lack of rapidity in the complete separation of the aqueous and organic phases from the heteroazeotrope.

The use of the n - heptane - benzene mixture has not completely solved the problem in view of the small amount of water as compared to the benzene driven away with the heteroazeotrope, having the effect of reducing substantially the efficiency of the process (see European Patent 1694).

With cyclohexane the results are improved; however, only the drying of alcohols containing 2 to 3 carbon atoms is considered (see European Patent 1681).

It has also been proposed to make use of heavy solvents to dry ethanol, particularly glycerin and glycols, preferably in association with salts ($CaCl_2$, $K_2CO_3$) so as to sufficiently increase the difference between the relative volatilities of the alcohols and water and to achieve the separation by extractive distillation. However, difficulties arise during the recuperation of the solvents, in view of the presence of salts which, under action of heat, form gums and tars and/or in view of their decomposition. This technique is thus limited to the drying of light alcohols, particularly ethanol (see USSR Patent 424854) and the required amounts of extraction solvent are often high.

Certain synthesis processes provide aliphatic alcohol mixtures relatively rich of methanol and ethanol but also containing alcohols of higher boiling point whose presence is beneficial for their use as components of a motor fuel.

As a matter of fact, they particularly improve the distillation curve and the compatibility with water. This is why it is advantageous to make use of alcohols as mixture instead of separately.

It has now been found that is possible to dehydrate a complex mixture of aliphatic alcohols containing at least one light alcohol and at least one heavy alcohol by subjecting the mixture to an extractive distillation in the presence of a selective solvent, followed with the azeotropic distillation of the obtained residue so as to obtain the dehydrated alcohols soluble in water, as distillate of the first distillation, and the alcohols insoluble in water in the distillate of the second distillation, as heteroazeotropes the two condensed phases of which are then distilled to obtain from the light phase the dehydrated heavy alcohols and from the heavy phase, water which is discharged.

By light alcohols it is meant alcohols having from 1 to 3 carbon atoms and by heavy alcohols: alcohols having 5 and/or 6 carbon atoms. Alcohols having 4 carbon atoms may also be present and considered as light or heavy alcohols depending on whether they are obtained at the top or at the bottom during the extractive distillation, in accordance with the nature of the solvent used.

Heavier alcohols are not excluded from the invention. However, they are more rarely found in substantial amounts in the products obtained by the above mentioned synthesis processes.

The selective solvents are defined as having at least one heteroatom in their molecule and being capable of dissolving at least 10% by weight of water or of each of the concerned alcohols.

EXAMPLES ARE:

Solvents of the glycol type, for example: ethylene-glycol, diethylene-glycol, triethylene-glycol, tetraethylene-glycol, propylene-glycol;

Solvents of the glycol ether type, for example: ethyleneglycol-monopropylether, ethyleneglycol-monobutylether;

Solvents of the diethyleneglycol - ether type, for example: diethyleneglycol - monomethylether, diethyleneglycol - monoethylether, diethyleneglycol-monobutylether, diethyleneglycol - dimethylether, or di- or tripropylene-glycolethers, for example di-propyleneglycolmethylether, tripropyleneglycolmethylether;

Solvents of the ethanolamine type, for example: mono- di- and triethanolamine;

N-methylpyrrolidone and sulfolane.

The process comprises several main steps:

A step (a) of extractive distillation wherein the aqueous mixture of aliphatic alcohols is introduced at an intermediary point of the distillation zone and the solvent at a point of said zone located above the point of introduction of the mixture, so as to obtain on the one hand a top product P consisting mainly of alcohols having in their molecules from 1 to 3, sometimes 4, carbon atoms (methanol, ethanol, propanol (n and iso) certain butanols), according to the nature of the solvent used, and containing substantially no water, said top product being discharged, and, on the other hand, a bottom product containing substantially the entirety of the introduced solvent and water and the heavy alcohols.

A step (b) of azeotropic distillation of the bottom product from step (a) wherein there is recovered, as residue, the solvent substantially freed from water, which is recycled to step (a) and, as distillate, the heteroazeotropic mixture, formed of water and heavy alcohols, which is condensed to obtain the separation thereof into two liquid phases, a heavy phase A of high water content and a light phase B of high heavy alcohol content, at least a portion of which may usefully be recycled, as reflux, in the azeotropic distillation column, each phase being subjected to distillation in a step (c) so as to obtain, as residues, respectively, from A a phase P containing essentially water, which is discharged, and from B a phase P' consisting of heavy alcohols freed from water, which is removed from the circuit, whereas the distillates are recycled to the heteroazeotropic mixture condensed in step (b).

The products P and P' are joined to form the mixture of dehydrated alcohols according to the invention for use as motor fuel in admixture with gasoline.

In an alternative embodiment of the process, the products P and P' may be subjected to conventional distillations for separately producing the desired alcohols.

The mixture of alcohols liable to be advantageously dehydrated according to the invention may contain, for example, from 2 to 70% by weight of water, generally from 15 to 50%. They contain light alcohols (methanol, ethanol, propanols) usually amounting to 50 to 80% by weight of the alcohol mixture itself, heavy alcohols (butanols, pentanols, hexanols) forming the complement. Other oxygenated compounds or higher alcohols may be present as mentioned above.

The accompanying drawing shows a simplified diagram of the process indicating how operates the installation.

The latter comprises an extractive distillation column $C_1$ and three distillation columns $C_2$, $C_3$ and $C_4$.

The mixture to be treated (water+alcohols) is introduced into column $C_1$ through line 1 and the extraction solvent through line 2. The distillation top fraction passes through line 3; it is condensed in exchanger 4; a portion thereof is recycled as reflux through line 5 and the other portion, issued from line 6 and consisting of light alcohols, is discharged from the installation.

Simultaneously, there is recovered, through line 7, a fraction containing essentially solvent, water and heavy alcohols, which is fed to column $C_2$ through said line for being separated into its constituents. There is recovered, through line 8, from the bottom of the column, the solvent substantially freed from water, which is fed back to column $C_1$, through line 2 (additional solvent may be introduced through 9), and through line 10, a distillate which is formed of the heteroazeotropic water-heavy mixture. After condensation in exchanger 11, the distillate passes through settler 12, where it is separated in two liquid phases. The light phase of high alcohol content is withdrawn through line 13; a portion is recycled, as reflux, through line 14 and the other portion is fed, through line 15, to the column $C_3$ where its constituents are separated; the heavy alcohols freed from water are recovered through line 16 and discharged from the installation whereas water, together with heavy alcohols, is conveyed through line 17 and, after condensation in exchanger 18, is fed back to the settler 12.

The heavy phase, of high water content, is withdrawn through line 19 and introduced into column $C_4$ to obtain, after distillation, at the bottom of the column, substantially pure water which is discharged from the installation through line 20 and, at the top of the column, a phase containing heavy alcohols and water which, through line 21, is fed to condenser 18.

A purge of the installation may be effected through line 22 whereby light constituents such as methanol, which may have been driven away, are recovered.

The withdrawn stream is fed to column $C_5$ wherefrom the light constituents are withdrawn through line 23, condensed in 24, partly recycled as reflux in column $C_5$, through line 25, and recovered through line 26 to be fed to line 1, and the water driving therewith small amounts of alcohols is conveyed through line 27 to be recycled to line 19.

EXAMPLE

In a distillation column of a 50 mm diameter, formed of 8 elements of 10 perforated downcomer-type trays, a boiler, a condenser and a reflux drum, there is introduced on the 38th plate from the bottom, a mixture of alcohols and water preheated at 60° C., at a rate of 750 g/h.

The detailed composition, in accordance with the number of carbon atoms in the molecule of these alcohols, is given in the second column of the table. On the 74th plate is introduced, at a rate of 2250 g/h, diethyleneglycol issued from the bottom of the solvent regeneration column and which contains as an average 300 ppm of water and 0.8% by weight of alcohols, mainly hexanol (composition given in the third column of the table).

The operation of the column is so regulated as to obtain the substantial entirety of the water at the bottom of the column, by establishing a reflux of distillate in a ratio of 0.65:1 with respect to the charge.

The top vapors of the column are condensed and supplied to the reflux drum; a portion is recycled therefrom to the column according to the above mentioned reflux rate whereas the other portion, corresponding to the production of dehydrated light alcohols, is discharged from the system. The composition by weight of said fraction of light alcohols is given in the 4th column of the table.

From the bottom of the column, there is withdrawn, through a valve controlled by means of a liquid level sensor in the boiler, a mixture which is fed to a buffer tank and then, through a pump, on to the 30th plate of the solvent regeneration column, which is identical to the first one but consists of 5 elements of 10 plates. This second column is so regulated as to reduce to less than 500 ppm the water content of the regenerated solvent which is withdrawn from the bottom at 242° C. and is recycled to the first column as above mentioned, after passage in a buffer tank. The top vapors, which are at a temperature of 97° C., are condensed and fed to a reflux drum which also acts as settler for separating the phase of high alcohol content from the phase of high water content. A portion of the alcohol phase (350 cc/h), is fed as reflux to the top of the column whereas the other portion is fed to the top of a column of 30 plates, which is so heated as to produce, at the bottom, heavy alcohols with a water content at most equal to 0.2% by weight. The top vapors of this column are condensed and fed back to the reflux-settler drum of the solvent regeneration column.

The aqueous phase issued from this reflux-settler drum is fed to the upper part of a fourth column, comprising 30 plates, so heated as to produce at the bottom water substantially free of alcohol, which is discharged from the system. The top vapors of said column are condensed and fed to the reflux-settler drum of the solvent regeneration column. The average composition by weight of the products is reported in columns 5 and 6 of the table.

TABLE I

COMPOSITION OF THE INPUTS-OUTPUTS OF THE SYSTEM (% by weight)

| Nature of the compounds | Charge column | Solvent column | Light alcohols | Heavy alcohols | Water |
|---|---|---|---|---|---|
| Methanol | 26.8 | — | 40.8 | — | — |
| Ethanol | 27.7 | — | 42.2 | — | — |
| Propanols | 10.5 | — | 15.8 | 0.9 | — |
| Butanols | 5.8 | — | 1.0 | 35.6 | — |
| Pentanols | 6.7 | — | — | 46.2 | Traces |
| Hexanols | 2.5 | 0.8 | — | 17.2 | Traces |
| Water | 20 | 300 ppm | 0.2 | 0.1 | 99.8 |
| Diethyleneglycol | — | 99.1 | — | — | — |

What is claimed is:

1. A process for producing dehydrated aliphatic alcohols from a mixture of light and heavy aliphatic alcohols with water, comprising the following steps of:
   (a) introducing the alcohols-water mixture into a first fractionation zone at an intermediary point thereof,
   (b) introducing a selective solvent at a point of the first fractionation zone above the point of introduction of the mixture,
   (c) withdrawing at the top a vapor effluent containing the dehydrated light aliphatic alcohols,
   (d) withdrawing from the bottom a liquid phase of high selective solvent content and containing water and heavy alcohols,
   (e) introducing said liquid phase into a second fractionation zone,
   (f) withdrawing at the top of the second factionation zone a vapor effluent consisting of an heteroazeotropic mixture of water with heavy alcohols,
   (g) withdrawing from the bottom of the second fractionation zone a liquid phase consisting of the selective solvent freed to a large extent of water and feeding it back to step (b),
   (h) condensing the hetero-azeotropic mixture of step (f) into two liquid phases, a light phase of high alcohol content and a heavy phase of increased water content and separating these two phases
   (i) withdrawing the light phase obtained in step (h) and feeding at least a fraction thereof into a third fractionation zone,
   (j) withdrawing at the top of the third fractionation zone a vapor effluent and feeding it back to step (h),
   (k) withdrawing from the bottom of the third fractionation zone a liquid phase consisting of dehydrated heavy aliphatic alcohols,
   (l) withdrawing the heavy phase obtained in step (h) and introducing at least a portion thereof into a fourth fractionation zone,
   (m) withdrawing at the top of the fourth fractionation zone a vapor effluent and feeding it back to step (h), and
   (n) recovering from the bottom of the fourth fractionation zone a liquid phase consisting essentially of water, 2. A process according to claim 1 comprising
   (a) withdrawing a remainder portion of the heavy phase of stop (h) and introducing it into a fifth fractionation zone,
   (b) withdrawing, at the top of the fifth fractionation zone, a vapor effluent and feeding it back to step (a),
   (c) recovering from the bottom of the fifth fractionation zone a liquid phase and feeding it back to step (l).

3. A process according to claim 1, wherein the mixture of aliphatic alcohols and water contains at least one alcohol having from 1 to 3 carbon atoms and at least one alcohol having 5 or 6 carbon atoms.

4. A process according to claim 1, wherein the mixture of aliphatic alcohols and water comprises alcohols having from 1 to 6 carbon atoms.

5. A process according to claim 1, wherein the selective solvent is a glycol or a glycol ether.

6. A process according to claim 1, wherein the selective solvent is an ethanolamine.

7. A process according to claim 1, wherein the selective solvent is N-methylpyrrolidone 8. A process according to claim 1, wherein the selective solvent is sulfolane.

9. A process according to claim 1, wherein the mixture of alcohols and water contains from 2 to 50% by weight of water.

10. A process according to claim 1, wherein the mixture of alcohols and water contains from 15 to 25% by weight of water.

* * * * *

UNITED STATES PATENT AND TRADEMARK OFFICE
CERTIFICATE OF CORRECTION

PATENT NO. : 4,366,032
DATED : December 28, 1982
INVENTOR(S) : PAUL MIKITENKO ET AL It is certified that error appears in the above-identified patent and that said Letters Patent is hereby corrected as shown below:

Column 5, line 33: reads "fractionation zone at an intermediary point thereof,"
should read -- fractionation zone at an intermediate point thereof, --

Column 5, line 46: reads "zone a vapor effluent consisting of an heteroazeo-"
should read -- zone a vapor effluent consisting essentially of an heteroazeo- --

Column 5, line 49: reads "tionation zone a liquid phase consisting of the selec- "
should read -- tionation zone a liquid phase consisting essentially of the selec- --

Column 6, line 11: reads "ation zone a liquid phase consisting of dehydrated"
should read -- ation zone a liquid phase consisting essentially of dehydrated --

Column 1, line 34, "The" should read -- An --.
Column 1, line 47, "the" should read -- a --.

Signed and Sealed this

Thirteenth Day of September 1983

[SEAL]

Attest:

GERALD J. MOSSINGHOFF

Attesting Officer   Commissioner of Patents and Trademarks